(12) United States Patent
Philbin et al.

(10) Patent No.: US 7,919,074 B2
(45) Date of Patent: Apr. 5, 2011

(54) POLYETHERAMIDE COMPOSITIONS

(75) Inventors: Michael Philbin, Hopewell, NJ (US); Carmine Iovine, Bridgewater, NJ (US); Jean-Pierre Leblanc, Hillsborough, NJ (US)

(73) Assignee: Akzo Nobel N.V., Arnhem (NL)

( * ) Notice: Subject to any disclaimer, the term of this patent is extended or adjusted under 35 U.S.C. 154(b) by 1325 days.

(21) Appl. No.: 11/419,010

(22) Filed: May 18, 2006

(65) Prior Publication Data

US 2007/0269396 A1    Nov. 22, 2007

(51) Int. Cl.
*A61Q 5/00* (2006.01)

(52) U.S. Cl. ....................... 424/70.17; 424/47

(58) Field of Classification Search .................. None
See application file for complete search history.

(56) References Cited

U.S. PATENT DOCUMENTS

| | | | |
|---|---|---|---|
| 3,157,681 A | 11/1964 | Fischer | |
| 3,734,874 A | 5/1973 | Kibler et al. | |
| 3,882,090 A | 5/1975 | Fagerburg et al. | |
| 4,133,803 A | 1/1979 | Klein | |
| 4,808,675 A | 2/1989 | Twilley et al. | |
| 5,053,484 A | 10/1991 | Speranza et al. | |
| 5,086,162 A | 2/1992 | Speranza et al. | |
| 5,118,785 A | 6/1992 | Speranza et al. | |
| 5,140,097 A | 8/1992 | Speranza et al. | |
| 5,158,762 A | 10/1992 | Pierce | |
| 5,324,812 A | 6/1994 | Speranza et al. | |
| 5,399,663 A | 3/1995 | Clark, II | |
| 5,744,570 A | 4/1998 | Gebben | |
| 5,837,802 A | 11/1998 | Van Lith et al. | |
| 5,846,524 A | 12/1998 | Breitenbach et al. | |
| 5,880,252 A | 3/1999 | Kim et al. | |
| 6,036,962 A | 3/2000 | Muller et al. | |
| 6,352,699 B1 * | 3/2002 | Mondet et al. | 424/401 |
| 6,368,583 B1 | 4/2002 | Kim et al. | |
| 6,641,804 B1 | 11/2003 | Ohta et al. | |
| 6,800,276 B2 | 10/2004 | Kim et al. | |
| 6,956,099 B2 | 10/2005 | Pavlin | |

FOREIGN PATENT DOCUMENTS

| | | |
|---|---|---|
| EP | 1068859 A1 | 1/2001 |
| GB | 1592189 | 7/1981 |
| WO | WO9614362 | 5/1996 |
| WO | WO2004083280 | 9/2004 |

OTHER PUBLICATIONS

Naval Stores—Production Chemistry and Utilization, D.F. Zinkel and J. Russell (eds.), Pulp Chem. Assoc. Inc., Chapter 23, pp. 780-799 (1989).
International Cosmetic Ingredient Dictionary and Handbook, T.E. Gottschalack and G. N. McEwen, Jr., Ph.D., J.D. editors, 10th Ed., vol. 4, pp. 2301-2402 (2003).
International Cosmetic Ingredient Dictionary and Handbook, T.E. Gottschalack and G. N. McEwen, Jr., Ph.D., J.D. editors, 10th Ed., vol. 4, pp. 2177-2299 (2003).

* cited by examiner

*Primary Examiner* — Jyothsna A Venkat
(74) *Attorney, Agent, or Firm* — James C. Abruzzo

(57) ABSTRACT

Ethanol soluble or dispersible polyetheramide polymers that have a percent elongation to break of less than 100%. The polymers are formed from a reaction mixture comprising at least one or more poly(alkyleneoxy) diamines and one or more diacids. The reaction mixture can optionally include one or more aliphatic diamines in addition to the one or more poly(alkyleneoxy) diamines. The polyetheramide polymers have application in personal care compositions such as hair fixative compositions, for example, hair spray formulations.

17 Claims, No Drawings

POLYETHERAMIDE COMPOSITIONS

BACKGROUND OF THE INVENTION

1. Technical Field

The present invention relates to alcohol soluble or dispersible polyether amide polymers. Further, the present invention is also directed towards the use of those polyetheramide polymers in personal care compositions.

2. Background Information

Personal care and cosmetic preparations have been used to improve people's appearance for centuries. Today, cosmetic preparations are widely used, with their formulations and functions being numerous and varied. To supply the performance and aesthetics desired, many of these cosmetic preparations contain various types of polymers. For example, polymers are used in skin care creams and lotions for different properties such as, among others, viscosity, flow, and emulsification. As a specific example in skin care, polymers are used in sunscreen formulations to provide rub-off resistance and waterproofing. In hair care products, polymers have been used for any number of properties including thickening, conditioning, emulsification, stability, and fixatives.

Polymer technologies continue to evolve to meet the changing needs of the cosmetic market. The quantity and types of polymer technologies vary greatly; however, there still exists areas yet to be explored and market needs left unaddressed.

In the case of hair fixative compositions, there has been a growing market need for hair fixative polymers that provide performance attributes of flexible hold, with a soft natural feel that has no adhesive tackiness, no raspiness and no brittle feel, while also providing humidity resistance, and be removable by shampoo. Most hair fixative compositions contain a film forming polymer that acts as a fixative, as well as a system for delivering that film-former, which is usually an alcohol or a mixture of alcohol and water. For aerosols, the delivery system will also contain a propellant.

Due to evolving environmental regulations controlling the emission of volatile organic components ("VOCs") into the atmosphere, water is being used to a greater degree in hair fixative compositions. As such, hair fixative polymers need to be able to function or be soluble in systems containing a range of alcohol, water and, in the case of aerosols, propellants, while providing the above mentioned performance attributes. Current hair fixatives do not provide this needed balance of properties.

Accordingly, there is a continued need for hair fixative polymers that provide the above mentioned performance attributes and solubility in hair fixative delivery systems.

SUMMARY OF THE INVENTION

It has now been discovered that polyetheramide polymers can be used in cosmetic hair care formulations with good performance and aesthetic results while meeting environmental and regulatory requirements. Performance benefits include smooth and soft feel, humidity resistance, low tack (all of which are useful attributes in skin care compositions), easy combing, low flake, moderate pH, and easy removal by shampooing.

According to the invention, there is provided alcohol soluble or dispersible polyetheramide polymers that have a percent elongation to break of less than 100%. In one embodiment, the polymers are made from a reaction mixture of poly(alkyleneoxy) diamine and a diacid, for example, adipic acid. In another embodiment, the reaction mixture also contains an aliphatic diamine.

The invention also provides for the use of those polyetheramide polymers in personal care compositions. Useful personal care composition applications include hair fixative compositions. Hair fixative compositions are understood in the art to include, for example, hair waxes, hair gels, hair mousses, aerosol hair sprays, non-aerosol hair sprays, and so forth. In one aspect, useful hair fixative compositions include hair spray formulations.

According to the present invention, useful polyetheramide polymers include the following structure—

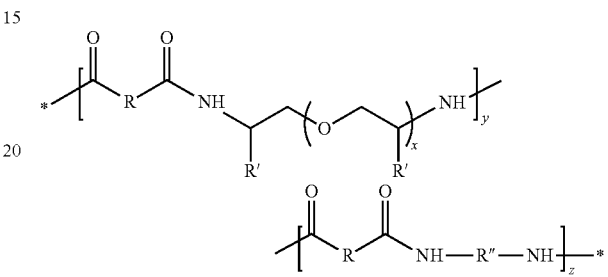

wherein R is aliphatic, cycloaliphatic or aromatic; R' is hydrogen or $CH_3$; R" is aliphatic, cycloaliphatic or aromatic; x is 2 to 34; y is 1 to 250; and z is 0 to 350. The polyetheramide polymer is formed from the reaction product of one or more dicarboxylic acids and one or more poly(alkyleneoxy) diamines, with the poly(alkyleneoxy) diamines comprising about 5 to 75 weight percent, based on total weight of the polyetheramide polymer. Further, the polyetheramide polymer has a percent elongation-to-break of less than 100%.

In one aspect, the poly(alkyleneoxy) diamine component of the above polyetheramide polymer has a number average molecular weight of from about 150 to about 2,000 Daltons ('Da').

In an optional embodiment, the polyetheramide polymer the reaction product used in polymerizing the polymer further includes one or more diamine components in addition to the poly(alkyleneoxy) diamine block component. Useful optional diamine components include, for example, 1,2-diaminocyclohexane, 1,4-diaminocyclohexane, hexamethylene diamine, ethylene diamine, phenylene diamine, xylylene diamine, 1,2-pentane diamine, ethylene diamine, 2-methyl penta-methylene diamine, isophorone diamine, or mixtures thereof.

In one aspect, polyetheramide polymers according to the present invention have a weight average molecular weight of from about 5,000 to about 70,000 Da.

In one aspect, polyetheramide polymers according to the present invention dissolve in an alcohol-water blend having a minimum weight percent alcohol of about 50 weight percent at 25° C.

In one aspect, the at least one or more dicarboxylic acid component of polyetheramide polymers according to the present invention is a diacid of the formula

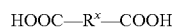

wherein Rx includes groups having 2 to 32 carbons. Examples of such diacids include 1,4-butanedioic acid (succinic acid), 1,6-hexanedioic acid (adipic acid), 1,7-heptanedioic acid (pimelic acid), 1,8-octanedioic acid (suberic acid), 1,9-nonanedioic acid (azelaic acid), 1,10-decanedioic acid (sebacic acid), 1,11-undecanedioic acid, 1,12-dodecanedioic acid (1,10-decanedicarboxylic acid), 1,13-tridecanedioic acid (brassylic acid) 1,14-tetradecanedioic acid (1,12-dodecanedicarboxylic acid), 1,4-cyclohexanedicarboxylic acid (CHDA), 1,3-cyclohexanedicarboxylic acid (CHDA), phthalic acid, polymerized fatty acids, or mixtures thereof.

The present invention is further directed towards personal care compositions that include at least the above-described polyetheramide polymers and a solvent. The polymer forms low viscosity solutions and/or dispersions of less than about 35 centipoise in solvent at about 6 weight percent polymer at about 25° C. The solvent is an alcohol or alcohol-water blend. In one aspect, the alcohol is ethanol.

In another aspect, the polymer used in the personal care compositions does not have a 100% modulus between about 8 and 40 kgf/cm$^2$.

In a further embodiment, the personal care composition is a hair fixative composition and the polymer provides curl retention of greater than about 30 percent after 2 hours at 21° C. (70° F.) and 90% humidity. In one aspect, the hair fixative composition is a hair spray composition. Hair spray compositions include both aerosol and non-aerosol.

In even another embodiment, the personal care composition is a hair fixative composition and the polymer provides a hair swatch stiffness of from about 0.005 to about 0.020 joules.

In one aspect, the one or more dicarboxylic acids useful in personal care compositions according to the present invention are selected from the group consisting of 1,4-cyclohexanedicarboxylic acid, 1,3-cyclohexanedicarboxylic acid and mixtures thereof.

The present invention also provides for a process for preparing a personal care composition involving the steps of reacting a mixture of from about 5 to about 85 weight percent of one or more poly(alkyleneoxy) diamines with from about 15 to about 95 weight percent of one or more diacids thereby forming a polyetheramide polymer, with weight percent based upon total weight percent of the polymer. The polyetheramide polymer is dissolved or dispersed in a solvent, wherein a 6 weight percent solution or dispersion of the resultant polyetheramide polymer in solvent at about 25° C. has a viscosity of less than about 35 centipoise. In one aspect, the solvent is alcohol. The reaction step can optionally further include reacting from about 5 to about 50 weight percent of one or more diamines in addition to the one or more poly (alkyleneoxy) diamines.

In a further step, the process for preparing the personal care composition includes dissolving or dispersing other additives in the solvent in addition to the polymer. Examples of those other additives include plasticizers, actives, neutralizers, colors or fragrances.

In one aspect, the process the reaction mixture used in forming the personal care composition does not have any mono-functional reactants that would react with either the amine or the acid groups.

DETAILED DESCRIPTION OF THE INVENTION

The following definitions are provided in order to aid in the description of the present invention:

"Cosmetic benefit" as used herein means a consumer recognized and/or perceived beneficial property.

"Dissolves in organic solvent" as used herein means that when a material is added to organic solvent or organic solvent is added to the material, the material combines with the organic solvent to form a solution or colloidal dispersion at concentration below about 15 weight percent based on weight of the material.

"Plasticizer" as used herein means any material that will contribute to making a film composition less brittle and more flexible.

"Solution" as used herein means a clear mixture (i.e., less than 10 NTUs turbidity at 5 weight percent polyetheramide) and includes colloidal dispersions.

"Surfactant" as used herein refers to an ingredient used in a cosmetic formulation that exhibits the ability to reduce interfacial tension between two immiscible substances, wet skin and hair surfaces, emulsify or solubilize oils, and/or suspend soil, and is meant to include amphoteric, anionic, cationic, and nonionic surfactants.

"Organic solvent" as used herein means a solvent having a C1 to C6 carbon chain with dipole moment and is meant to include solvents such as ethanol.

"Aqueous solvent" as used herein means a solvent containing at least 2 percent water based on total weight of solvent.

"Non-aqueous solvent" and "anhydrous solvent" as used herein means a solvent containing less than 2 percent water based on total weight of solvent.

"Solvent" as used herein means any liquid that, at 25° C., will at least partially dissolve another liquid or a solid.

"Cosmetic ingredient" as used herein means any ingredient that can be used in cosmetic and/or personal care formulations.

"Hair fixative polymer" as used herein means any film forming polymer that, when dissolved or dispersed and applied to the hair, will fix the hair shafts in a given conformation. Hair fixative polymers include natural polymers, synthetic polymers and combinations thereof, and can be anionic, cationic, nonionic, amphoteric or betaine polymers. Hair fixative polymers can be used either alone or in combination with other natural and/or synthetic polymers. Hair fixative products include, but are not limited to, mousses, gels, hair sprays (pump and aerosol), waxes and so forth.

"Hair Spray" means a product sprayed on hair and intended to hold the hair in a desired conformation.

"Hair spray polymer" means a hair fixative polymer that forms low viscosity solutions or dispersions in organic solvent at typical dosages in a hair spray formulation, or thins upon shear to give low enough viscosity such that the polymer, solvent, any other additives, propellants, and/or hair spray ingredients can be sprayed onto the hair using an aerosol or non-aerosol spray device and dry to fix the hair in a conformation.

"Mousse" as used herein means a personal care product in which the ingredients foam when dispensed from a container without any mechanical action from the user except possibly the shaking of the product in the container prior to actuation of a valve and subsequent dispensing of the internal contents by actuation.

"Reaction mixture" refers to all those chemicals and their amounts used to form a polymer. For instance, a polymer may be prepared by reacting chemicals "a" and "b", and then adding chemical "c" to the reaction product(s) of chemicals "a" and "b" (the reaction products may be abbreviated as "ab" for convenience). The reaction mixture, as used herein, refers to a hypothetical mixture of chemicals "a", "b" and "c" even though each of those chemicals may be not present together at any one time because chemicals "a" and "b" reacted to form a product ("ab") and therefore are not present when chemical "c" is added to the reaction flask. Solvents may be present during the formation of the polymer; however, because solvents do not become incorporated into the structure of the polymer, solvents are not included within the term "reaction mixture".

"Residue" as used herein means a material that is exuded from a film upon drying that causes a film to become tacky and block.

"PAODA" as used herein means poly(alkyleneoxy) diamine.

"Personal care composition" as used herein means a composition intended to be applied to hair or skin in order to provide a cosmetic benefit.

"Polyetheramide polymer" means a macromolecule containing both polyamide and polyether sections.

"Polyamide" as used herein means a macromolecule containing a plurality of amide groups (i.e., groups of the formula —NR—C(=O)— and/or —C(=O)—NR—), where R is hydrogen, an aliphatic, cycloaliphatic or aromatic group.

Polyamides as a class of polymer are well known in the art and are commonly prepared via a condensation polymerization process whereby diamines are reacted with dicarboxylic acid compounds (diacids). As discussed below, polymers according to the present invention are also prepared by reacting diamines with diacids.

"Polyether" as used herein means polyether groups, also referred to herein as poly(alkylene oxide) groups. The structure of polyether groups may also be represented as —(O—R—)$_n$—, where "n" represents a number of repeating O—R groups, wherein R represents alkylene groups and O is oxygen.

Polyethers as a class of polymers are also well known in the art. For example, one type of polyether is commonly prepared by reacting an alkylene oxide (e.g., ethylene oxide) with an initiating group (e.g., methanol). Presently, many polyethers are commercially available having terminating groups selected from amine, hydroxyl and carboxylic acid. Polyethers having two amine-terminating groups are used in the present invention to introduce polyether blocks into a polyamide polymer. This approach provides blocks of polyether groups within a polyamide polymer. It has been discovered that polymers having this structure are useful as hair fixative polymers, for example, as hair spray polymers.

6 weight percent polymer and 25° C.) in a hair spray formulation to permit application to the hair by spraying from an aerosol or non-aerosol hair spray using commercially available spray valves and spray pumps.

Chemical structures of polymers according to the present invention are further described below and can be represented as follows—

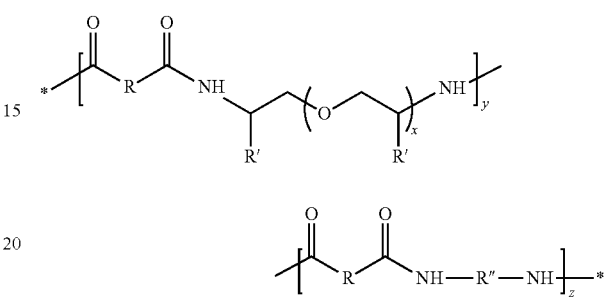

wherein R and R" are independently aliphatic, cycloaliphatic or aromatic; R' is hydrogen or methyl; x, y and z are integer values representing the number of repeat units, and x is 2 to 34; y is 1 to 250; and z is 0 to 350.

As seen from the above structure, in polyetheramide polymers according to the present invention, nearest amide groups are separated by either alkylene, arylene or polyether groups (i.e., poly(alkyleneoxy) groups). Polyetheramide polymers according to the present invention contain at least one internal polyether group (i.e., a polyether group that is flanked by two amide groups).

In general terms, polyetheramide polymers according to the present invention are prepared by reacting a polyoxyalkylene diamine and, optionally, an aliphatic diamine, with a dicarboxylic acid according to the following reaction—

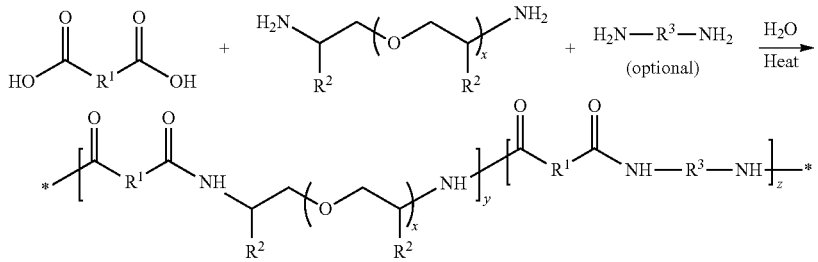

Polyetheramide polymers according to the present invention contain a polyether block, and, more specifically, a polyether block flanked by two amide groups. In one aspect of the invention, two amide groups of the polyetheramide polymer also flank a hydrocarbon group. Inventive polymers containing this particular combination of groups (i.e., polyether and alkylene diradicals) have been found to function as hair fixative polymers, and, in particular, hair spray polymers. However, in order for the polyetheramide polymers to be effective hair spray polymers, it is necessary that the polymers be able to form low viscosity solutions and/or dispersions (i.e., less than about 35 centipoise in alcohol or alcohol-water blends at wherein $R^1$ and $R^3$ are aliphatic, cycloaliphatic, or aromatic; $R^2$ is hydrogen or methyl; x, y and z are integer values representing the number of repeat units, and x is 2 to 34; y is 1 to 250; and z is 0 to 350.

Polymers according to the present invention are formed from an amount of poly(alkyleneoxy) diamine (PAODA) that is effective in providing flexibility and shampoo removability when applied to hair in a hair fixative formulation. Polymers formed without enough of the PAODA constituent form films that are too brittle for holding hair and too difficult to remove with shampooing and therefore are not effective. In addition to this lower limit, there is also an upper limit to the weight percentage of PAODA that may be added to the reaction mixture when forming the polymers of the invention while still obtaining adequate performance in hair fixative formulations. Specifically, polymers made with too much PAODA have poor humidity resistance and on-hair stiffness properties and therefore are not effective. Further, this upper limit of PAODA in the reaction mixture used in forming the polymer of the present invention depends upon the molecular weight of PAODA used and the diacid used in the reaction mixture. For example, greater amounts of lower molecular weight than higher molecular weight PAODA can be added to form polymers according to the present invention before performance of the polymer as a hair fixative begins to fail. Accordingly, an "effective" amount of the polymer can vary based upon the type of diacid and/or diamine used in forming the polymer, as well as the molecular weight of the diamine.

Accordingly, in one embodiment of the invention polyetheramide polymers are formed by a reaction mixture containing from about 5 to about 75 weight percent poly(alkyleneoxy) diamine (PAODA). In another embodiment polyetheramide polymers are formed by a reaction mixture containing from about 5 to 71 weight percent PAODA. In even another embodiment, polyetheramide polymers are formed by a reaction mixture containing from about 5 weight percent to about 50 weight percent PAODA. In another embodiment, polyetheramide polymers are formed by a reaction mixture containing from about 5 weight percent to about 40 weight percent PAODA; in another embodiment, from about 5 weight percent to about 30 weight percent PAODA; in another embodiment, from about 5 weight percent to about 25 weight percent PAODA; and in another embodiment, from about 5 weight percent to about 20 weight percent PAODA.

Techniques for preparing PAODA are well known in the art and include reacting an initiator containing two hydroxyl groups with ethylene oxide and/or mono-substituted ethylene oxide, followed by conversion of the resulting terminal hydroxyl groups to amines. Illustrative PAODA reactants employed herein include the JEFFAMINE® brand of poly(alkyleneoxy) amines available from Huntsman LLC (Salt Lake City, Utah, USA). These PAODAs are prepared by reacting bifunctional initiators with ethylene oxide and propylene oxide, followed by conversion of terminal hydroxyl groups to amines.

Exemplary PAODAs include the XTJ and JEFFAMINE® D-series poly(alkyleneoxy) diamines from Huntsman, which have a number average molecular weight ('Mn') between about 150 and about 2,000 Da. Useful PAODAs include those having an Mn of at least about 230 to about 400 Da, and are exemplified by JEFFAMINE® D-230 and JEFFAMINE® D-400 PAODAs. When the molecular weight of the PAODA is above about 2000 Da, the tackiness, viscosity, and/or humidity resistance of the corresponding polyetheramide becomes undesirable for the polyetheramide to function as a hair fixative polymer. In one aspect, the PAODA can have more than two amine groups.

In addition to PAODA, polymers according to the present invention are formed from one or more diacids or multifunctional acids. As used herein, a diacid is a compound of the formula $HOOC-R^x-COOH$, where $R^x$ includes groups having 2-32 carbons. Suitable diacids have a linear, cyclic or aromatic $C_{4-12}$ hydrocarbon group between the two carboxylic acid groups. Linear diacids suitable for the present invention include 1,4-butanedioic acid (succinic acid), 1,6-hexanedioic acid (adipic acid), 1,7-heptanedioic acid (pimelic acid), 1,8-octanedioic acid (suberic acid), 1,9-nonanedioic acid (azelaic acid), 1,10-decanedioic acid (sebacic acid), 1,11-undecanedoic acid, 1,12-dodecanedioic acid (1,10-decanedicarboxylic acid), 1,13-tridecanedioic acid (brassylic acid) and 1,14-tetradecanedioic acid (1,12-dodecanedicarboxylic acid). Cyclic aliphatic diacids suitable for the present invention include 1,4-cyclohexanedicarboxylic acid (CHDA) and 1,3-cyclohexanedicarboxylic acid (CHDA).

Another exemplary diacid useful in the present invention is the reaction product of acrylic or methacrylic acid (or the ester thereof, with a subsequent hydrolysis step to form an acid) and an unsaturated fatty acid. For example, a $C_{21}$ diacid of this type can be formed by reacting acrylic acid with a $C_{18}$ unsaturated fatty acid (e.g., oleic acid), where an ene-reaction presumably occurs between the reactants. An exemplary $C_{21}$ diacid is DIACID® 1550 (commercially available from MeadWestvaco Corporation, Stamford, Conn., USA).

Aromatic diacids can also be used in forming the polymers of the present invention. "Aromatic diacids" as used herein refers to molecules having two carboxylic acid groups (—COOH) or reactive equivalents thereof (e.g., acid chloride (—COCl) or ester (—COOR)) and at least one aromatic ring ("Ar"). Phthalic acids, for example, isophthalic acid and terephthalic acid, are exemplary aromatic diacids. The aromatic diacid can contain aliphatic carbons bonded to the aromatic ring(s), such as $HOOC-CH_2-Ar-CH_2-COOH$ and the like. The aromatic diacid can contain two aromatic rings joined together through one or more carbon bonds, (e.g., biphenyl with carboxylic acid substitution) or fused together (e.g., naphthalene with carboxylic acid substitution).

Useful diacids further include polymerized fatty acid, also referred to as dimer acid. Polymerized fatty acid is typically a mixture of structures, where individual dimer acids may be saturated, unsaturated, cyclic, acyclic, etc. Thus, a detailed characterization of the structure of dimer acid is not readily available. However, good discussions of fatty acid polymerization may be found in, for example, U.S. Pat. No. 3,157,681 and NAVAL STORES—PRODUCTION, CHEMISTRY AND UTILIZATION, D. F. Zinkel and J. Russell (eds.), Pulp. Chem. Assoc. Inc., Chpt. 23 (1989). Typical unsaturated fatty acids used to form polymerized fatty acid include oleic acid, linoleic acid, linolenic acid, etc. Tall oil fatty acid (a mixture containing long-chain unsaturated fatty acids obtained as a byproduct of the wood pulping process) is an exemplary source of polymerized fatty acid useful in the invention. Alternatively, polymerized fatty acid may be prepared by polymerization of unsaturated fatty acids from other sources (e.g., soybeans or canola). Thus, polymerized fatty acid typically contains 30-42 carbon atoms and may be described as having the structure of dimer or trimer acids. Dimer fatty acids are available commercially, for example, under the trade names UNIDYME® and SYL-VADYME™ dimer acids (Arizona Chemical, Jacksonville, Fla.), EMPOL® dimer acids (Cognis, Ambler, Pa.); and PRIPOL® dimer acids (Uniqema, New Castle, Del.).

In the polymerization of fatty acids, both dimer and trimer acids are typically produced. The polymerization product can be subjected to distillation in order to remove all or most of the monomeric fatty acid species, as well as fractionate the dimer and trimer acids. However, it is difficult and expensive to fractionate polymerized fatty acids to where they contain no trimer acid and/or no residual monomeric fatty acid. Accordingly, commercially available "dimer acid" often contains some trimer acid and/or monomeric acid, and the specification sheet for the product typically list a trimer acid and/or monomeric acid content. Thus, dimer acids used in preparing polymers according to the present invention may contain some trimer acid and/or monomeric acid.

In one aspect, the dimer acid from polymerized fatty acid contains less than about 25 wt % trimer acid. In other various aspects of the invention the dimer acid contains less than 20 wt %, or less than 15 wt %, or less than 10 wt %, or less than 5 wt % trimer acid. Also, in one aspect the dimer acid contains less than about 25 wt % residual monomeric acid. In other various aspects of the invention, the dimer acid contains less than 20 wt %, or less than 15 wt %, or less than 10 wt %, or less than 5 wt % monomeric fatty acid.

The ratio of monomeric fatty acid, dimer acid and trimer acid present in a polymerized fatty acid distillate can be determined by gas chromatography according to methods well known in the art. Preferably, the amount of dimer acid present in reaction mixtures used to prepare polymers according to the present invention is such that less than about 10% of the total acid equivalents in this mixture, or less than about 25% of the total weight of this mixture, comes from dimer acid.

The type and dosage of diacid in the reaction mixture should be balanced with the type and quantity of the PAODA in order to achieve optimum hair fixative properties and solubility of the polymer of the present invention. For example, when a higher molecular weight PAODA is included in the reaction mixture, a diacid that gives a higher glass transition temperature ('Tg') polymer can be chosen to increase the on-hair stiffness of the resulting polymer. (Glass transition temperature is determined according to the procedure described in the EXAMPLES section below.) Likewise, when a lower molecular weight or lower dosage of PAODA is included in the reaction mixture, then a diacid that gives a lower Tg to the polymer can be used for the same reason.

As used herein, the terms diacid and poly(alkyleneoxy) diamine refer to both the chemicals per se as well as reactive equivalents thereof. For example, reactive equivalents of 1,4-cyclohexane dicarboxylic acid include the corresponding salt forms, acid halides and short-chain esters. Reactive equivalents of poly(alkyleneoxy) diamine include the corresponding salt forms and short-chain amides. Either the chemicals per se or their reactive equivalents may be used to prepare polyetheramide polymers according to the present invention.

In addition to the PAODA and the one or more diacids, the reaction mixture used in forming polymers according to the present invention can optionally contain one or more additional diamines or multi-functional amines. These additional diamines can provide performance properties to the polymer that balance those provided by the different types and quantities of PAODA and diacid included in the reaction mixture used in forming the polymers.

When one or more diamines in addition to PAODA are included in the reaction mixture, the one or more additional diamine(s) can be $C_2$-$C_{12}$ aliphatic diamines. In another embodiment, these additional diamines are cyclic. Examples of optional diamines useful in the present invention include 1,2-diaminocyclohexane, 1,4-diaminocyclohexane, hexamethylene diamine, ethylene diamine, phenylene diamine, xylylene diamine, 1,2-pentane diamine, ethylene diamine, 2-methyl penta-methylene diamine, and isophorone diamine.

In terms of weight percent, in one embodiment additional diamine(s) comprise from 0 to about 50 weight percent based on total weight percent of the polyetheramide polymer; in another embodiment, from 0 to about 45 weight percent based on total weight percent of the polyetheramide polymer; and in even another embodiment from 0 to about 25 weight percent based on total weight percent of the polyetheramide polymer.

In one aspect, the polymer of the invention can be defined by the total weight percent of diamine (PAODA plus any additional diamine compounds) present in reaction mixture to form the polymer. In one embodiment of the polymer of the present invention, the total weight percent of diamine present in the reaction mixture used in forming the polymer is from about 20 weight percent to about 85 weight percent; in another embodiment the diamine is from about 40 weight percent to about 80 weight percent; in another embodiment, the total diamine weight percent is from about 50 to about 75 weight percent.

Polymers according to the present invention require no special terminal groups (i.e., the polymers need not be terminated by an ester group, tertiary amide group, or poly(alkyleneoxy)-substituted amide). They may, then, be of high molecular weight, have residual acid groups as termini or residual amine groups as termini. The only restriction is that the polymer be able to function as a hair fixative polymer. That is, at typical dosages in hair fixative formulations, polymers according to the invention must form a solution or dispersion in alcohol (e.g., ethanol) and/or alcohol-water blends; provide a viscosity in alcohol and/or alcohol-water blends such that the mixture can be sprayed with adequate aesthetics; form a film on hair which is removable with shampooing; and fix the hair in a given conformation.

Polymers according to the present invention have no particular restriction with respect to molecular weight; however typical weight average molecular weights (Mw) range from about 5,000 to about 70,000 Da. In another aspect, weight average molecular weights range from about 5,000 to about 50,000 Da. In even another aspect, weight average molecular weights of the polymer range from about 10,000 to about 35,000 Da. In another aspect, weight average molecular weights of the polymers range from about 15,000 to about 35,000 Da.

The polymers of the present can be characterized by their solubility in alcohol (e.g., ethanol). In one aspect of the invention, the polymers dissolve in an alcohol-water blend at some minimum weight percent alcohol in an alcohol-water blend at 25° C. In one embodiment, 5 weight percent polymer will dissolve in an alcohol-water blend at 25° C. and having a minimum weight percent of alcohol of about 10 percent; in another embodiment, the minimum weight percent of alcohol is about 15; in another embodiment, the minimum weight percent of ethanol is about 20; in another embodiment, the minimum weight percent of alcohol is about 30; in another embodiment, the minimum weight percent of alcohol is about 40; in another embodiment, the minimum weight percent of alcohol is about 50; in another embodiment, the minimum weight percent of alcohol is about 60; in another embodiment, the minimum weight percent of alcohol is about 70; in another embodiment, the minimum weight percent of alcohol is about 80.

In one aspect of the invention, the reaction mixture that is used to prepare the polyether amide polymer does not have any mono-functional reactants added (except minor amounts as impurities in the di-functional reactants) that would react with either amine or carboxylic acid groups. In other words, stating that the reaction mixture does not contain any mono-functional compound reactive with acid or amine groups is not intended to mean that each of the components of the reaction mixture must be 100% pure and cannot contain trace amounts of mono-functional compound reactive with acid or amine groups.

In another embodiment, the reaction mixture used to prepare the polyetheramide polymer includes some small amount of mono-functional reactants purposefully added to the mixture to influence the performance properties of the resulting polymer. For instance, mono-functional reactants may be added to control molecular weight or to influence solubility or durability of the resin films cast from the polymer.

In another aspect of the invention, the di-functional reactants may also contain some amount of multifunctional compound (i.e., more than two functional groups). For instance, a component added to the reaction mixture as a diamine may also contain some triamine, and a component added to the reaction mixture as a diacid may also contain some triacid. In additional embodiments of the invention, additional multifunctional amine or acid is added to the reaction mixture to influence the properties of the resulting polymer.

The relative amount of diacid, PAODA and optional diamine is important in preparing a polyetheramide polymer. When the polymer of the present invention is used in a hair spray formulation, it is important that the balance of PAODA, diacid, and optional additional diamine gives viscosity in alcohol and/or alcohol-water blends that provides acceptable spray aesthetics, as well as provides humidity resistance, shampoo removability, good on-hair properties (e.g., stiffness, raspiness, tack, and low flake or residue) and combing properties. One skilled in the art will know viscosity and performance requirements for hair spray polymer solutions and/or dispersions and how to modify valve dimensions to optimize spray properties.

The reaction mixture that is prepared in order to form a polyetheramide polymer according to the present invention will have both PAODA and diacid, and, as previously noted, may have other optionally present reactants. For example, the PAODA may be optionally combined with one or more additional diamines, and, independently, the diacid may be a mixture of diacids. In those instances where there is additional diamines and/or a diacid mixture, the relative amounts of diamine in the mixture of diamine and the relative amounts of diacid in the mixture of diacid may be characterized in terms of equivalent(s) and/or equivalent percent, or in terms of weight percent.

Polymers according to the present invention are useful as hair fixative polymers and can be defined by the amount of high humidity curl retention the polymer provides in hair fixative formulations. "High humidity Curl Retention" is determined according the procedure explained in the EXAMPLES section below. In one embodiment of the invention, high humidity curl retention provided by polymers according to the present invention is greater than 20 percent after 2 hours at 70° F. and 90% humidity. In one embodiment of the invention, high humidity curl retention provided by polymers according to the present invention is greater than 30 percent after 2 hours at 70° F. and 90% humidity. In another embodiment of the invention, high humidity curl retention is greater than 40 percent after 2 hours at 70° F. and 90% humidity. In a further embodiment, high humidity curl retention is greater than 50% after 2 hours at 70° F. and 90% humidity. In even another embodiment, high humidity curl retention is greater than 60% after 2 hours at 70° F. and 90% humidity. In another embodiment, high humidity curl retention is greater than 70% after 2 hours at 70° F. and 90% humidity. In another embodiment, high humidity curl retention is greater than 80% after 2 hours at 70° F. and 90% humidity. In another embodiment, high humidity curl retention is greater than 90% after 2 hours at 70° F. and 90% humidity.

Polymers according to the present invention can also be defined by the hair swatch stiffness the polymer provides in hair spray formulations. "Hair Swatch Stiffness" is determined according to the Diastron Hair Swatch Stiffness Procedure detailed in the EXAMPLES section below. In one embodiment, the hair spray polymer provides hair swatch stiffness up to about 0.020 joules; in another embodiment the hair spray polymer provides hair swatch stiffness from about 0.005 to about 0.020 joules; and in even another embodiment the hair spray polymer provides hair swatch stiffness from about 0.005 to about 0.015 joules. Polyetheramide polymers within these ranges of swatch stiffness have excellent hair fixative properties.

Polymers according to the present invention can further be defined by their viscosity in alcohol (particularly, ethanol) at 25° C. In one embodiment of the invention, a 6 weight percent solution or dispersion of the polymer of the invention in alcohol at 25° C. has a viscosity less than about 35 centipoise. In another embodiment, the viscosity of a 6 weight percent solution is less than about 30 centipoise. In even another embodiment, the viscosity is less than about 25 centipoise; and in another embodiment, the viscosity is less than about 20 centipoise. Viscosity measurements discussed herein were determined using a Brookfield RVTD Viscometer with low viscosity attachment.

When used as a hair fixative polymer, polymers according to the present invention can be defined by the tensile elastic modulus (Young's modulus) of a film formed from the polymer. The modulus of elasticity (or stiffness) was determined according to the "Tensile Testing" procedure detailed in the EXAMPLES section below. In one embodiment of the invention, the polymer does not have a 100% modulus between 8 and 40 $kgf/cm^2$. ("100% modulus" refers to the stress of the sample at 100% elongation. Polymers according to the present invention break before they elongate 100%.) In one embodiment of the invention, the polymer has a Young's modulus from about 20 $kgf/cm^2$ to about 1400 $kgf/cm^2$; in another embodiment, the polymer has a modulus from about 45 $kgf/cm^2$ to about 1400 $kgf/cm^2$; in another embodiment, the polymer has a modulus from about 50 $kgf/cm^2$ to about 1400 $kgf/cm^2$. In another embodiment, the polymers of the invention have no measurable Young's modulus because the dogbone samples could not be mounted into the tensile tester due to the samples being too soft or too brittle. Polymers according to the invention meeting the modulus parameters provide excellent hair fixative properties.

Further, in one embodiment polymers according to the present invention have a percent elongation to break of less than 100%. ("Percent elongation to break" is determined by the length of the sample at break less the original length of the sample, the result of which is divided by the original sample length and multiplied by 100.) In even another embodiment, inventive polyetheramide polymers have a percent elongation to break or less than about 70%. In another embodiment, polyetheramide polymers according to the present invention have a percent elongation to break of less than about 50%. In even another embodiment, inventive polyetheramide polymers have a percent elongation to break or less than about 40%. In another embodiment, inventive polyetheramide polymers have a percent elongation to break or less than about 35%; and in another embodiment, the percent elongation to break is about 33% or less. In another embodiment, polymers according to the invention have no measurable elongation. Measurement of elongation is determined according to the "Tensile Testing" procedure detailed in the Examples section below.

As described herein, polymers of the present invention perform well as hair fixatives. In one embodiment, the polymers are used in hair fixative formulations. In another aspect, the polymers are used in hair spray formulations. Typically, in formulating a hair spray, the hair spray polymer is dissolved or dispersed in a solvent along with other additives such as plasticizers, actives, neutralizers, colors and fragrances. After the solution or dispersion of all ingredients is complete, the resulting solution or concentrate is filled into packaging and equipped with either a non-aerosol spray pump or an aerosol valve. If the hair spray is an aerosol, the packaging must also be filled with propellant (which can be soluble, insoluble or partially soluble). Other types of dispensing systems include bag-in-can and diaphragm. With bag-in-can systems, propellant (gas or liquid) is filled between the outer packaging shell and an inner bag, which is filled the hair spray concentrate. The pressure of the propellant presses on the inner bag to dispense the concentrate when the actuator is depressed. In diaphragm systems, the hair spray concentrate is forced into and expands an elastic diaphragm sleeve which fits within the outer packaging shell. The concentrate is forced out of the packaging by the constriction of the sleeve when the actuator is depressed.

As noted above, hair fixative compositions include a solvent. The solvent is typically water, an alcohol such as ethanol, or blends thereof. Additional solvents have also been used in hair sprays, including chlorinated and fluorinated solvents such as dichloroethane and chlorofluorocarbon P-12, other low molecular weight alcohols such as methanol and propanol, low molecular weight alkanes such as pentane and hexane, and petroleum distillates.

In one aspect according to the present invention, the solvent is ethanol. In another embodiment of the invention, hair fixatives according to the present invention contain some minimum weight percent ethanol based on weight of the composition. In yet another embodiment, hair fixatives according to the invention contains from about 10 to about 98 weight percent ethanol; in another embodiment from about 20 to about 95 weight percent ethanol; in another embodiment from about 30 to about 90 weight percent ethanol; in another embodiment from about 40 to 90 weight percent ethanol; in another embodiment from about 50 to about 80 weight percent ethanol; in another embodiment from about 50 to about 70 weight percent ethanol; in another embodiment from about 55 to about 65 weight percent ethanol.

The weight percent of polymer in a hair fixative composition can vary depending upon the level of hold and other properties desired. Typically, the weight percent of polymer can vary from about 0.5 to about 6 weight percent based on total weight of the formulation (including propellant in the case of an aerosol hair spray). However, some commercial hair sprays contain as high as 12 weight percent polymer based on total weight of the hair spray formulation.

Accordingly, the amount of polymer in hair fixatives according to the present invention can vary from about 0.5 to about 12 weight percent based on total weight of the composition. In another embodiment, the amount of polymer in the hair fixative composition can vary from about 0.5 to about 10 weight percent based on total weight of the composition. In another embodiment, the amount of polymer in the hair fixative composition can vary from about 0.5 to about 7 weight percent; in even another embodiment, the amount of polymer in the hair fixative composition can vary from about 0.5 to about 5 weight percent; and in another embodiment, the amount of polymer in the hair fixative composition can vary from about 1 to about 4 weight percent.

In aerosol hair sprays, a propellant is also added to the formulation. Examples of propellants include low molecular weight hydrocarbons such as propane and butane, alkoxides such as dimethyl ether (i.e., DYMEL® A from DuPont), chlorofluorocarbons and hydrofluorocarbons such as CFC P-12 and 1,1-difluoroethane (i.e., DYMEL® 152a from DuPont). In some cases, the propellant also offers some solvency to the hair spray polymer and other ingredients, such as with dimethyl ether. Depending upon the type and amount of propellant in the hair spray formulation, pressure in an aerosol hair spray can vary from about 17 psi to about 108 psi at room temperature. In one embodiment of the hair spray composition of the present invention, the propellant is chosen to give a pressure from about 17 to about 108 psi at room temperature; in another embodiment of the hair spray of the invention, the pressure is from about 31 to about 70 psi; in another embodiment of the hair spray of the invention, the pressure is from about 40 to 65; in another embodiment of the invention, the pressure is from about 40 to about 55 psi.

The hair fixative formulation may also contain additional additives known in the art. These optional ingredients include, without limitation, thickeners, emulsifiers, aesthetic modifiers, UV filters, humectants (such as hydroxyethyl urea, available from National Starch and Chemical Company under the trademark HYDROVANCE®), lubricants, silicones, de-viscosifying agents, moisturizers, emollients, solvents, chelating agents, vitamins, antioxidants, botanical extracts, pH adjusting agents, preservatives, fragrances, waterproofing agents, active ingredients (anti-aging agents, firming or toning agents, etc.), dyes, pigments, colors, polymers, conditioning agents, rheology modifiers, surfactants, opacifiers, foaming agents, heat generating agents, glitter and decorative beads and shapes.

Hair fixative formulations according to the present invention may optionally also contain plasticizers know in the art. Such plasticizing agents include, without limitation, dimethicone copolyols, polyols, polycarboxylic acids, and polyesters. Examples of useful dimethicone copolyols include, but are not limited to PEG-12 Dimethicone, PEG/PPG-18/18 Dimethicone, and PPG-12 Dimethicone. Examples of useful polyols include, but are not limited to ethylene glycol, propylene glycol, sugar alcohols such as sorbitol, mannitol, maltitol, lactitol; mono-di- and oligosaccharides such as fructose, glucose, sucrose, maltose, lactose, and high fructose corn syrup solids and ascorbic acid. Examples of polycarboxylic acids include, but are not limited to, citric acid, maleic acid, succinic acid, polyacrylic acid, and polymaleic acid. Examples of polyesters include, but are not limited to, glycerol triacetate, acetylated-monoglyceride, diethyl phthalate, triethyl citrate, tributyl citrate, acetyl triethyl citrate, acetyl tributyl citrate.

Other examples of plasticizers include, but are not limited to mineral oils, vegetable oils, triglycerides, lanolins and their derivatives, unsaturated fatty acids and their derivatives, silicones, and some emollients; humectants such as glycerol, sorbitol, lactates (including but not limited to sodium, ammonium, and potassium salts), polyols (e.g., propylene glycol), polyethylene glycol (200-600), and Sorbeth-30; natural moisturizing factors (NMFs) such as urea, lactic acid, and sodium pyrrolidone carboxylic acid (PCA); liposomes, natural and vegetal moisturizing agents such as glycerol, serine, chitosan PCA, sodium hyaluronate, hyaluronic acid, microsponges, soluble collagen, modified protein, monosodium L-glutamate, lecithins and phospholipids and their derivatives; alpha and beta hydroxy acids such as glycolic acid, lactic acid, citric acid, maleic acid and salicylic acid; polymeric plasticizers such as polysaccharides and their derivatives, polyacrylates, and polyquaterniums; and proteins and amino acids such as glutamic acid, aspartic acid, and lysine.

Plasticizers will be present in a plasticizing effective amount. In one embodiment, the plasticizer will be present in the hair spray formulation in an amount from about 0 to about 2 weight percent based on total weight of the hair fixative composition. In yet another embodiment, the plasticizer will be present in an amount from about 0.10 to about 1 weight percent based on total weight of the hair fixative composition; and in yet another embodiment, the plasticizer will be present in an amount from about 0.10 to about 0.5 weight percent based upon total weight of the hair fixative composition.

Polyetheramide polymers of the present invention are compatible with other polymers commonly used in personal care formulations. Examples of such polymers include, but are not limited to, the following: from National Starch and Chemical Company, AMPHOMER® and AMPHOMER® LV-71 polymers (octyl acrylamide/acrylates/butyl aminoethyl methacrylate polymer), AMPHOMER® HC polymer (acrylates/octyl acrylamide polymer) BALANCE® 0/55 and BALANCE® CR polymers (acrylates polymer), BALANCE® 47 polymer (octyl acrylamide/butyl aminoethyl methacrylate polymer), DERMACRYL® 79 and DERMACRYL® LT polymers (acrylates/octyl acrylamide polymer), RESYN 28-2930 polymer (VA/crotonates/vinyl neodecanoate polymer), RESYN® 28-1310 polymer (VA/crotonates polymer), FLEXAN® polymers (sodium polystyrene sulfonate), DynamX® polymer (polyurethane-14 (and) AMP-Acrylates polymer), RESYN® XP polymer (acrylates/octylacrylamide polymer), STRUCTURE® 2001 (acrylates/steareth-20 itaconate polymer) and STRUCTURE® 3001 (acrylates/ceteth-20 itaconate polymer); from ISP, OMNIREZ™-2000 (PVM/MA half ethyl ester polymer), GANEX® P-904 (butylated PVP), GANEX® V-216 (PVP/hexadecene polymer) GANEX® V-220 (PVP/eicosene polymer), GANEX® WP-660 (tricontanyl PVP), GANTREZ™ A-425 (butyl ester of PVM/MA polymer), GANTREZ™ AN-119 PVM/MA polymer, GANTREZ™ ES 225 (ethyl ester of PVM/MA polymer), GANTREZ™ ES-425 (butyl ester of PVM/MA polymer), GAFFIX® VC-713 (vinyl caprolactam/PVP/dimethylaminoethyl methacrylate polymer), GAFQUAT™ 755 (polyquaternium-11), GAFQUAT™ HS-100 (polyquaternium-28) AQUAFLEX® XL-30 (polyimide-1), AQUAFLEX SF-40 (PVP/vinylcaprolactam/DMAPA Acrylates polymer), AQUAFLEX® FX-64 (isobutylene/ethylmaleimide/hydroxyethyl maleimide polymer), ALLIANZ™ LT-120 (acrylates/C1-2 succinates/hydroxyacrylates polymer), STYLEZE® CC-10 (PVP/DMAPA acrylates polymer), STYLEZE® 2000 (VP/acrylates/lauryl methacrylate polymer), STYLEZE® W-20 (polyquaternium-55), Polymer Series (PVP/dimethylaminoethylmethacrylate polymer), ADVANTAGE™ S and ADVANTAGE™ LCA (vinylcaprolactam/VP/dimethylaminoethyl methacrylate polymer), ADVANTAGE™ PLUS (VA/butyl maleate/isobornyl acrylate polymer); from BASF, ULTRAHOLD® STRONG (acrylic acid/ethyl acrylate/t-butyl acrylamide), LUVIMER® 100P (t-butyl acrylate/ethyl acrylate/methacrylic acid), LUVIMER® 36D (ethyl acrylate/t-butyl acrylate/methacrylic acid), LUVIQUAT™ HM-552 (polyquaternium-16), LUVIQUAT™ HOLD (polyquaternium-16), LUVISKOL® K30 (PVP) LUVISKOL® K90 (PVP), LUVISKOL® VA 64 (PVP/VA polymer) LUVISKOL® VA73W (PVP/VA polymer), LUVISKOL® VA, LUVISET® PUR (polyurethane-1), LUVISET® Clear (VP/methacrylamide/vinyl imidazole polymer), LUVIFLEX® SOFT (acrylates polymer), ULTRAHOLD® 8 (acrylates/acrylamide polymer), LUVISKOL® Plus (polyvinylcaprolactam), LUVIFLEX® Silk (PEG/PPG-25/25 dimethicone/acrylates polymer); from Amerchol, AMERHOLD™ DR-25 (acrylic acid/methacrylic acid/acrylates/methacrylates); from Rohm and Haas Company, ACUDYNE® 258 (acrylic acid/methacrylic acid/acrylates/methacrylates/hydroxy ester acrylates, ACUDYNE® 180 (Acrylates/Hydroxyesters Acrylates Polymer), ACUDYNE® SCP (ethylenecarboxyamide/AMPSA/methacrylates polymer), and the ACULYN® rheological modifiers; from Mitsubishi and distributed by Clariant, DIAFORMER® Z-301, DIAFORMER® Z-SM, and DIAFORMER® Z-400 (methacryloyl ethyl betaine/acrylates polymer); from ONDEO Nalco, FIXOMER® A-30 and FIXOMER® N-28 (INCI names: methacrylic acid/sodium acrylamidomethyl propane sulfonate polymer); from Noveon, FIXATE® G-100 (AMP-acrylates/allyl methacrylate polymer), FIXATE® PLUS (polyacrylates-X), CARBOPOL® Ultrez 10 (Carbomer), CARBOPOL® Ultrez 20 (acrylates/$C_{10-30}$ alkyl acrylates polymer), AVALURE® AC series (acrylates polymer), AVALURE® UR series (polyurethane-2, polyurethane-4, PPG-17/IPDI/DMPA polymer); polyethylene glycol; water-soluble acrylics; water-soluble polyesters; polyacrylamides; polyamines; polyquaternary amines; styrene maleic anhydride (SMA) resin; polyethylene amine; and other conventional polymers.

Examples of commercial starches along with their INCI names with which the polyetheramide polymers of the present invention may be used include but are not limited to the following: from National Starch and Chemical Company, the AMAZE® polymer (corn starch modified), CELQUAT® LS-50 resin (polyquaternium-4/hydroxypropyl starch polymer), STRUCTURE® XL polymer (hydroxypropyl starch phosphate), DRY FLO®PC lubricant (aluminum starch octenyl succinate), DRY FLO®AF lubricant (corn starch modified), DRY FLO® ELITE LL lubricant (aluminum starch octenyl succinate (and) lauryl lysine), DRY FLO® ELITE BN lubricant (INCI name: aluminum starch octenyl succinate (and) boron nitride), PURITY 21C starch (zea mays (corn) starch), TAPIOCA™ PURE (tapioca starch), NATRASORB® W and NATRASORB® BATH (tapioca starch), NATRASORB® HFB (aluminum starch octenyl succinate (and) acrylates polymer (and) magnesium carbonate), INDEX™ (dextrin), thermally inhibited corn, potato, tapioca, high amylase, and waxy maize starches sold under the NOVATION® trademark, and resistant starches sold under the HI-MAIZE® trademark; from the Croda Company, CROSTYLE™ MFP (trimethyl quaternized maize starch); from ONDEO Nalco, SENSOMER® C1-50 (starch hydroxypropyl trimonium chloride).

Other natural polymers with which the polyetheramide polymer of the present invention may be used include, without limitation, the following: cellulosic materials such as carboxymethyl cellulose, hydroxypropyl cellulose, microcrystalline cellulose, ethylcellulose, cellulose acetate phthalate, cationic cellulose derivatives such as polyquaternium-4 (CELQUAT® L-200 and CELQUAT® H-100 polymers from National Starch and Chemical Company) and polyquaternium-10 (CELQUAT® SC-240C and CELQUAT® 230M polymers from National Starch and Chemical Company); gums such as xanthan gum (AMAZE™ XT polymer from National Starch and Chemical Company); pullulan; hydrocolloids; carrageenan; alginate; casein; gelatin; and solubilized proteins.

As discussed above, the properties of polyetheramide polymers according to the present invention make them well suited as fixatives and film formers in many hair care applications. Additional personal care compositions in which the polyetheramide polymers of the present invention may be suited include the following: hair makeup removers, daily facial wash, facial masks or packs, scrub cleansers, foaming cleansers, moisturizing cleansers, shower gels, body washes, bar soaps, dissolvable soap sheets, anti-acne products, and anti-aging products, aftershave lotions, baby lotions/oils/powders/creams, baby shampoo, basecoats and undercoats, bath capsules, bath oils/tablets/salts, bath soaps and detergents, beard softeners, blushers, body and hand preparations, bubble baths, cleansing products, colognes and toilet waters, cuticle softeners, deodorants depilatories, eye lotions, eye makeup preparations, eye makeup removers, eye shadows, eyebrow pencils, eyeliners, face and neck preparations, face powders, foot powders and sprays, foundations, fragrance preparations, hair bleaches, hair color sprays, hair coloring preparations, hair conditioners, hair dyes and colors, hair lighteners with color, hair preparations, hair rinses, hair shampoos, hair sprays, hair straighteners, hair tints, hair wave sets, indoor tanning preparations, leg and body paints, lipsticks, makeup bases, makeup fixatives, makeup preparations, manicuring preparations, mascara, men's talcum, moisturizing preparations, nail creams and lotions, nail extenders, nail polish and enamel removers, nail polish and enamels, night skin care preparations, paste masks, perfumes, permanent waves, personal cleanliness products, powders, preshave lotions, rouges, sachets, shampoos, shaving cream, shaving preparations, shaving soap, skin care preparations, skin fresheners, suntan gels/creams/lotions, suntan preparations, tonics, dressings and other hair grooming aids, among others. Specific examples of ingredients typically used in these specific applications can be found in the INTERNATIONAL COSMETIC INGREDIENT DICTIONARY AND HANDBOOK, T. E. Gottschalck and G. N. McEwen, Jr., Ph.D., J. D. editors, 10$^{th}$ ed., Vol. 4, pp. 2301-2402, The Cosmetic, Toiletry, and Fragrance Association, Washington, D.C. (2003).

Personal care applications in which polyetheramide polymers according to the present invention may be used may also may contain the following optional ingredients: abrasives, absorbents, adhesives, anti-acne agents, anti-caking agents, anti-caries agents, antidandruff agents, antifoaming agents, antifungal agents, antimicrobial agents, antioxidants, antiperspirant agents, antistatic agents, artificial nail builders, beads, binders, buffering agents, bulking agents, chelating agents, colorants, corn/callus/wart removers, corrosion inhibitors, cosmetic astringents, cosmetic biocides, denaturants, deodorant agents, depilating agents, drug astringents (skin protectant drugs), emulsion stabilizers, epilating agents, exfoliants, external analgesics, film formers, flavoring agents, fragrance ingredients, hair colorants, hair conditioning agents, hair fixatives, hair-waving/straightening agents, humectants, lytic agents, nail conditioning agents, opacifying agents, oral care agents, oral health care drugs, oxidizing agents, pesticides, pH adjusters, plasticizers, preservatives, propellants, reducing agents, skin bleaching agents, skin-conditioning agents (emollient, humectant, occlusive), skin protectants, slip modifiers, solvents, sunscreen agents, surface modifiers, surfactants (cleansing agents, emulsifying agents, foam boosters, hydrotropes, solubilizing agents, suspending agents), suspending agents (nonsurfactant), ultraviolet light absorbers, viscosity controlling agents, viscosity decreasing agents, viscosity increasing agents (aqueous and nonaqueous), water-proofing agents, heat generating agents and/or effervescing agents, glitter and decorative beads and shapes. Specific examples of ingredients typically used for these functions can be found in the INTERNATIONAL COSMETIC INGREDIENT DICTIONARY AND HANDBOOK (INCI), T. E. Gottschalck and G. N. McEwen, Jr., Ph.D., J. D. editors, 10$^{th}$ ed., Vol. 4, pp. 2177-2299, The Cosmetic, Toiletry, and Fragrance Association, Washington, D.C. (2003). Polyether amide polymers of the present invention can also be used in products in different forms such as gels, lotions, creams, emulsions, liquids, pastes, solids, sticks, bars, sprays, films or sheets, among others.

EXAMPLES

The following examples are presented to further illustrate and explain the present invention and should not be taken as limiting in any regard. All percents used are on a weight/weight basis.

Example 1

Synthesis of a Polyetheramide Polymer Comprising 36.1 Wt % PAODA and 45.6 wt % Diacid 207.4 g of water was added to a 2000 mL reaction vessel equipped with an agitator, heating mantle, distillation head, and nitrogen purge. While stirring, the water was purged subsurface with nitrogen for approximately 10 minutes, with the purge continued during addition of the remaining reagents. 57.0 g (0.50 moles, 18.3 wt %) of 1,2-diaminocyclohexane, 112.4 g (0.50 moles, 36.1 wt %) of polyoxypropylene diamine (PAODA) having a Mn of about 230 g/mol (available as JEFFAMINE® D-230 from Huntsman Corporation, Salt Lake City, Utah, USA), 141.8 g (0.97 moles, 45.6 wt %) of adipic acid, and 0.62 g of 50% aqueous hypo-phosphorous acid (as catalyst and anti-oxidant) were then added to the stirred aqueous solution. The subsurface nitrogen purge was changed so that the reaction was continued under a blanket of nitrogen. The reaction mixture was heated to 190° C. Once all the water had distilled off, the reaction was continued at 190° C. for 20 hours, and then poured off.

Example 2

Synthesis of a Polyetheramide Polymer Comprising 61.3 wt % PAODA and 38.7 wt % Diacid 244.3 g of water was added to a 2000 mL reaction vessel equipped with an agitator, heating mantle, distillation head, and nitrogen purge. While stirring, the water was purged subsurface with nitrogen for approximately 10 minutes, with the purge continued during addition of the remaining reagents. 224.7 g (1.00 mole, 61.3 wt %) of JEFFAMINE® D-230, 141.8 g (0.97 moles, 38.7 wt %) of adipic acid, and 0.73 g of 50% aqueous hypo-phosphorous acid were then added to the stirred aqueous solution. The subsurface nitrogen purge was changed so that the reaction was continued under a blanket of nitrogen. The reaction mixture was heated to 190° C. Once all the water had distilled off, the reaction was continued at 190° C. for 20 hours and then poured off.

Example 3

Synthesis of a Polyetheramide Polymer Comprising 58.2 wt % PAODA and 41.8 wt % Diacid 257.2 g of water was added to a 2000 mL reaction vessel equipped with an agitator, heating mantle, distillation head, and nitrogen purge. While stirring, the water was purged subsurface with nitrogen for approximately 10 minutes, with the purge continued during addition of the remaining reagents. 224.7 g (1.00 mole, 58.2 wt %) of PAODA (JEFFAMINE® D-230) and 161.1 g (1.00 mole, 41.8 wt %) of terephthalic acid were added to the aqueous solution. The subsurface nitrogen purge was changed so that the reaction continued under a blanket of nitrogen. The reaction mixture was heated to 240° C. Once all the water had distilled off, the reaction was continued at 240° C. for 5 hours and then poured off.

Example 4

Synthesis of a Polyetheramide Polymer Comprising 49.6 wt % PAODA and 41.8 wt % Diacid 226.2 g of water was added to a 2000 mL reaction vessel equipped with an agitator, heating mantle, distillation head, and nitrogen purge. While stirring, the water was purged subsurface with nitrogen for approximately 10 minutes, with the purge continued during addition of the remaining reagents. 168.5 g (0.75 moles, 49.6 wt %) of PAODA (JEFFAMINE® D-230), 29.1 g (0.25 moles, 8.6 wt %) of hexamethylene diamine, 141.8 g (0.97 moles, 41.8 wt %) of adipic acid, and 1.7 g of phenolic antioxidant and phosphite as stabilizer (IRGANOX® B1171, commercially available from Ciba Specialty Chemicals) were added to the stirred aqueous solution. The subsurface nitrogen purge was changed so that the reaction continued under a blanket of nitrogen. The reaction mixture was heated to 190° C. Once all the water had distilled off, the reaction was continued at 190° C. for 20 hours and then poured off.

Example 5

Synthesis of a polyetheramide polymer comprising 7.0 wt % PAODA and 45.4 wt % Diacid 214.6 g of water was added to a 2000 mL reaction vessel equipped with an agitator, heating mantle, distillation head, and nitrogen purge was added. While stirring, the water was purged subsurface with nitrogen for approximately 10 minutes, with the purge continued during addition of the remaining reagents. 22.5 g (0.10 moles, 7.0 wt %) of JEFFAMINE® D-230, 153.3 g (0.90 moles, 47.6 wt %) of isophorone diamine, 146.1 g (1.00 moles, 45.4 wt %) of adipic acid, and 0.64 g of 50% aqueous hypo-phosphorous acid were added to the stirred aqueous solution. The subsurface nitrogen purged was changed so that the reaction continued under a blanket of nitrogen. The reaction mixture was heated to 190° C. Once all the water had distilled off, the reaction was continued at 190° C. for 8 hours and then poured off.

Example 6

Synthesis of a polyetheramide polymer comprising 10.5 wt % PAODA and 44.4 wt % Diacid 214.0 g of water was added to a 2000 mL reaction vessel equipped with an agitator, heating mantle, distillation head, and nitrogen purge. While stirring, the water was purged subsurface with nitrogen for approximately 10 minutes, with the purge continued during addition of the remaining reagents. 33.7 g (0.15 moles, 10.5 wt %) of PAODA (JEFFAMINE® D-230), 144.8 g (0.85 moles, 45.1 wt %) of isophorone diamine, 142.5 g (0.98 moles, 44.4 wt %) of adipic acid, and 0.32 g of 50% aqueous hypo-phosphorous acid were added to the stirred aqueous solution. The subsurface nitrogen purge was changed so that the reaction continued under a blanket of nitrogen. The reaction mixture was heated to 190° C. Once all the water had distilled off, the reaction was continued at 190° C. for 3 hours and then poured off.

Example 7

Synthesis of a Polyetheramide Polymer Comprising 13.7 wt % PAODA and 44.7 wt % Diacid 218.2 g of water was added to a 2000 mL reaction vessel equipped with an agitator, heating mantle, distillation head, and nitrogen purge. While stirring, the water was purged subsurface with nitrogen for approximately 10 minutes, with the purge continued during addition of the remaining reagents. 44.9 g (0.20 moles, 13.7 wt %) of PAODA (JEFFAMINE® D-230), 136.2 g (0.80 moles, 41.6 wt %) of isophorone diamine, 146.1 g (1.00 moles, 44.7 wt %) of adipic acid, and 0.33 g of 50% aqueous hypo-phosphorous acid were added to the stirred aqueous solution. The subsurface nitrogen purge was changed so that the reaction continued under a blanket of nitrogen. The reaction mixture was heated to 190° C. Once all the water had distilled off, the reaction was continued at 190° C. for 4 hours and then poured off.

Example 8

Synthesis of a Polyetheramide Polymer Comprising 17.0 wt % PAODA and 44.3 wt % Diacid 220.0 g of water was added to a 2000 mL reaction vessel equipped with an agitator, heating mantle, distillation head, and nitrogen purge. While stirring, the water was purged subsurface with nitrogen for approximately 10 minutes, with the purge continued during addition of the remaining reagents. 56.2 g (0.25 moles, 17.0 wt %) of PAODA (JEFFAMINE® D-230), 127.7 g (0.75 moles, 38.7 wt %) of isophorone diamine, 146.1 g (1.00 moles, 44.3 wt %) of adipic acid, and 0.33 g of 50% aqueous hypo-phosphorous acid were added to the stirred aqueous solution. The subsurface nitrogen purged was changed so that the reaction was continued under a blanket of nitrogen. The reaction mixture was heated to 190° C. Once all the water had distilled off, the reaction was continued at 190° C. for 4 hours and then poured off.

Example 9

Synthesis of a Polyetheramide Polymer Comprising 32.7 wt % PAODA and 42.5 wt % Diacid 229.1 g of water was added to a 2000 mL reaction vessel equipped with an agitator, heating mantle, distillation head, and nitrogen purge. While stirring, the water was purged subsurface with nitrogen for approximately 10 minutes, with the purge continued during addition of the remaining reagents. 112.4 g (0.50 moles, 32.7 wt %) of PAODA (JEFFAMINE® D-230), 85.2 g (0.50 moles, 24.8 wt %) of isophorone diamine, 146.1 g (1.00 moles, 42.5 wt %) of adipic acid, and 0.69 g of 50% aqueous hypo-phosphorous acid were added to the stirred aqueous solution. The subsurface nitrogen purge was changed so that the reaction continued under a blanket of nitrogen. The reaction mixture was heated to 190° C. Once all the water had distilled off, the reaction was continued at 190° C. for 18 hours and then poured off.

Example 10

Synthesis of a Polyetheramide Polymer Comprising 11.8 wt % PAODA and 43.1 wt % Diacid 181.0 g of water was added to a 2000 mL reaction vessel equipped with an agitator, heating mantle, distillation head, and nitrogen purge. While stirring, the water was purged subsurface with nitrogen for approximately 10 minutes, with the subsurface nitrogen purge continued during addition of the remaining reagents. 32.0 g (0.08 moles, 11.8 wt %) of polyoxypropylene diamine having a Mn of about 400 g/mol (available as JEFFAMINE® D-400 from Huntsman Corporation, Salt Lake City, Utah), 122.6 g (0.72 moles, 45.1 wt %)

of isophorone diamine, 116.9 g (0.80 moles, 43.1 wt %) of adipic acid, and 0.54 g of 50% aqueous hypo-phosphorous acid were added to the stirred aqueous solution. The subsurface nitrogen purge was changed so that the reaction continued under a blanket of nitrogen. The reaction mixture was heated to 190° C. Once all the water had distilled off, the reaction was continued at 190° C. for 18 hours and then poured off.

Example 11

Synthesis of a Polyetheramide Polymer Comprising 42.7 wt % PAODA and 39.0 wt % Diacid 199.8 g of water was added to a 2000 mL reaction vessel equipped with an agitator, heating mantle, distillation head, and nitrogen purge. While stirring, the water was purged subsurface with nitrogen for approximately 10 minutes, with the subsurface nitrogen purge continued during addition of the remaining reagents. 128.0 g (0.32 moles, 42.7 wt %) of PAODA (JEFFAMINE® D-400), 54.7 g (0.48 moles, 18.3 wt %) of 1,2-diaminocyclohexane, 116.9 g (0.80 moles, 39.0 wt %) of adipic acid, and 0.60 g of 50% aqueous hypo-phosphorous acid were added to the stirred aqueous solution. The subsurface nitrogen purge was changed so that the reaction continued under a blanket of nitrogen. The reaction mixture was heated to 190° C. Once all the water had distilled off, the reaction was continued at 190° C. for 20 hours and then poured off.

Example 12

Synthesis of a Polyetheramide Polymer Comprising 59.3 wt % PAODA and 18.7 wt % Diacid 202.2 g of water was added to a 2000 mL reaction vessel equipped with an agitator, heating mantle, distillation head, and nitrogen purge. While stirring, the water was purged subsurface with nitrogen for approximately 10 minutes, with the subsurface nitrogen purge continued during addition of the remaining reagents. 179.8 g (0.80 moles, 59.3 wt %) of PAODA (JEFFAMINE® D-230), 66.8 g (0.39 moles, 22.0 wt %) of 1,4-cyclohexane dicarboxylic acid, 56.7 g (0.39 moles, 18.7 wt %) of adipic acid, and 0.30 g of 50% aqueous hypo-phosphorous acid were added to the stirred aqueous solution. The subsurface nitrogen purge was changed so that the reaction continued under a blanket of nitrogen. The reaction mixture was heated to 240° C. Once all the water had distilled off, the reaction was continued at 240° C. for 5 hours and then poured off.

Example 13

Synthesis of a Polyetheramide Polymer Comprising 58.3 wt % PAODA and 41.7 wt % Diacid 205.6 g of water was added to a 2000 mL reaction vessel equipped with an agitator, heating mantle, distillation head, and nitrogen purge. While stirring, the water was purged subsurface with nitrogen for approximately 10 minutes, with the subsurface nitrogen purge continued during addition of the remaining reagents. 179.8 g (0.80 moles, 58.3 wt %) of PAODA (JEFFAMINE® D-230), 100.2 g (0.58 moles, 9.2 wt %) of 1,4-cyclohexane dicarboxylic acid, 28.4 g (0.19 moles, 41.7 wt %) of adipic acid, and 0.31 g of 50% aqueous hypo-phosphorous acid were added to the stirred aqueous solution. The subsurface nitrogen purge was changed so that the reaction continued under a blanket of nitrogen. The reaction mixture was heated to 240° C. Once all the water had distilled off, the reaction was continued at 240° C. for 5 hours and then poured off.

Example 14

Synthesis of a Polyetheramide Polymer Comprising 57.4 wt % PAODA and 42.6 wt % Diacid 208.9 g of water was added to a 2000 mL reaction vessel equipped with an agitator, mantle, distillation head, and nitrogen purge. While stirring, the water was purged subsurface with nitrogen for approximately 10 minutes, with the subsurface nitrogen purge continued during addition of the remaining reagents. 179.8 g (0.80 moles, 57.4 wt %) of PAODA (JEFFAMINE® D-230), 133.6 g (0.78 moles, 42.6 wt %) of 1,4-cyclohexane dicarboxylic acid, and 0.31 g of 50% aqueous hypo-phosphorous acid were added to the stirred aqueous solution. The subsurface nitrogen purge was changed so that the reaction continued under a blanket of nitrogen. The reaction mixture was heated to 240° C. Once all the water had distilled off, the reaction was continued at 240° C. for 5 hours and then poured off.

Example 15

Synthesis of a Polyetheramide Polymer Comprising 62.6 wt % PAODA and 37.4 wt % Diacid 200.3 g of water was added to a 2000 mL reaction vessel equipped with an agitator, heating mantle, distillation head, and nitrogen purge. While stirring, the water was purged subsurface with nitrogen for approximately 10 minutes, with the subsurface nitrogen purge continued during addition of the remaining reagents. 118.0 g (0.53 moles, 39.3 wt %) of PAODA (JEFFAMINE® D-230), 70.0 g (0.18 moles, 23.3 wt %) of JEFFAMINE® D-400, 87.7 g (0.51 moles, 29.2 wt %) of 1,4-cyclohexane dicarboxylic acid, 24.8 g (0.17 moles, 8.2 wt %) of adipic acid, and 0.30 g of 50% aqueous hypo-phosphorous acid were added to the stirred aqueous solution. The subsurface nitrogen purge was changed so that the reaction continued under a blanket of nitrogen. The reaction mixture was heated to 240° C. Once all the water had distilled off, the reaction was continued at 240° C. for 5 hours and then poured off.

Example 16

Synthesis of a Polyetheramide Polymer Comprising 66.9 wt % PAODA and 33.1 wt % Diacid 202.3 g of water was added to a 2000 mL reaction vessel equipped with an agitator, heating mantle, distillation head, and nitrogen purge. While stirring, the water was purged subsurface with nitrogen for approximately 10 minutes, with the subsurface nitrogen purge continued during addition of the remaining reagents. 73.0 g (0.33 moles, 24.1 wt %) of PAODA (JEFFAMINE® D-230), 130.0 g (0.33 moles, 42.8 wt %) of PAODA (JEFFAMINE® D-400), 54.3 g (0.32 moles, 17.9 wt %) of 1,4-cyclohexane dicarboxylic acid, 46.1 g (0.32 moles, 15.2 wt %) of adipic acid, and 0.30 g of 50% aqueous hypo-phosphorous acid were added to the stirred aqueous solution. The subsurface nitrogen purge was changed so that the reaction continued under a blanket of nitrogen. The reaction mixture was heated to 240° C. Once all

Example 17

Synthesis of a Polyetheramide Polymer Comprising 72.2 wt % PAODA and 27.8 wt % Diacid 203.3 g of water was added to a 2000 mL reaction vessel equipped with an agitator, heating mantle, distillation head, and nitrogen purge. While stirring, the water was purged subsurface with nitrogen for approximately 10 minutes, with the subsurface nitrogen purge continued during addition of the remaining reagents. 220.0 g (0.55 moles, 72.2 wt %) of PAODA (JEFFAMINE® D-400), 45.9 g (0.27 moles, 15.0 wt %) of 1,4-cyclohexane dicarboxylic acid, 39.0 g (0.27 moles, 12.8 wt %) of adipic acid, and 0.30 g of 50% aqueous hypo-phosphorous acid were then added to the stirred aqueous solution. The subsurface nitrogen purge was changed so that the reaction was continued under a blanket of nitrogen. The reaction mixture was heated to 240° C. Once all the water had distilled off, the reaction was continued at 240° C. for 5 hours and then poured off.

Example 18

Synthesis of a Polyetheramide Polymer Comprising 71.3 wt % PAODA and 28.7 wt % Diacid 205.6 g of water was added to a 2000 mL reaction vessel equipped with an agitator, heating mantle, distillation head, and nitrogen purge. While stirring, the water was purged subsurface with nitrogen for approximately 10 minutes, with the subsurface nitrogen purge continued during addition of the remaining reagents. 220.0 g (0.55 moles, 71.3 wt %) of PAODA (JEFFAMINE® D-400), 68.9 g (0.40 moles, 22.4 wt %) of 1,4-cyclohexane dicarboxylic acid, 19.5 g (0.13 moles, 6.3 wt %) of adipic acid, and 0.31 g of 50% aqueous hypo-phosphorous acid were then added to the stirred aqueous solution. The subsurface nitrogen purge was changed so that the reaction was continued under a blanket of nitrogen. The reaction was heated to 240° C. under a blanket of nitrogen. Once all the water had distilled off, the reaction was continued at 240° C. for 4 hours and then poured off.

Example 19

Synthesis of a Polyetheramide Polymer Comprising 70.5 wt % PAODA and 29.5 wt % Diacid 207.9 g of water was added to a 2000 mL reaction vessel equipped with an agitator, heating mantle, distillation head, and a nitrogen purge. While stirring, the water was purged subsurface with nitrogen for approximately 10 minutes, with the subsurface nitrogen purge continued during addition of the remaining reagents. 220.0 g (0.55 moles, 70.5 wt %) of PAODA (JEFFAMINE® D-400), 91.9 g (0.53 moles, 29.5 wt %) of 1,4-cyclohexane dicarboxylic acid, and 0.31 g of 50% aqueous hypo-phosphorous acid were then added to the stirred aqueous solution. The subsurface nitrogen purge was changed so that the reaction continued under a blanket of nitrogen. The reaction mixture was heated to 240° C. Once all the water had distilled off, the reaction was continued at 240° C. for 4 hours and then poured off.

Comparative Example 1

Example 6 of U.S. Pat. No. 6,956,099

149.5 g (0.08 moles, 46.0 wt %) of JEFFAMINE® D-2000 (polyoxypropylene diamine having a Mn of about 2000 g/mol, commercially available from Huntsman Corporation, Salt Lake City, Utah, USA), 120.3 g (0.21 moles, 37.0 wt %) of VERSAMINE® 551 ($C_{36}$ dimer diamine commercially available from Henkel KGaA, Düsseldorf, Germany), 55.3 g (0.32 moles, 17.0 wt %) of 1,4-cyclohexane dicarboxylic acid (CHDA), and 0.3 g of 50% aqueous hypo-phosphorous acid were added to a 2000 mL reaction vessel equipped with an agitator, heating mantle, distillation head, and nitrogen purge. The reaction mixture was heated over about 2 hours to 220° C. while being stirred under a vigorous stream of nitrogen, and held at this temperature for an additional 4 hours, then poured off.

Comparative Example 2

Example 7 of U.S. Pat. No. 6,956,099

75.0 g (0.33 moles, 25.0 wt %) of JEFFAMINE® D-230, 135.0 g (0.24 moles, 45.0 wt %) of Versamine 551, 27.0 g (0.16 moles, 9.0 wt %) of 1,4-cyclohexane dicarboxylic acid, 54.0 g (0.37 moles, 18.0 wt %) of adipic acid, 9.0 g (0.03 moles, 3.0 wt %) isostearic acid, and 0.3 g of 50% aqueous hypo-phosphorous acid were added to a 2000 mL reaction vessel equipped with an agitator, heating mantle, distillation head, and nitrogen purge. The reaction mixture was heated over about 2 hours to 220° C. while being stirred under a vigorous stream of nitrogen, and held at this temperature for an additional 4 hours, then poured off.

TABLE 1

POLYMER COMPOSITION

| Polymer | Equivalent % of total amine equivalents | | | | | | | wt % | wt % |
| --- | --- | --- | --- | --- | --- | --- | --- | --- | --- |
| | Jeffamine D230 | Jeffamine D400 | Jeffamine D2000 | DCH-99 | HMDA | IPDA | Versamine 551 | wt % PAODA | aliphatic diamine |
| Example 1 | 50% | | | 50% | | | | 36.1% | 18.3% |
| Example 2 | 100% | | | | | | | 61.3% | |
| Example 3 | | 100% | | | | | | 58.2% | |
| Example 4 | 25% | | | | 75% | | | 49.6% | 8.6% |
| Example 5 | 10% | | | | | 90% | | 7.0% | 47.6% |
| Example 6 | 15% | | | | | 85% | | 10.5% | 45.1% |
| Example 7 | 20% | | | | | 80% | | 13.7% | 41.6% |

TABLE 1-continued

POLYMER COMPOSITION

| | | | | | | |
|---|---|---|---|---|---|---|
| Example 8 | 25% | | | 75% | 17.0% | 38.7% |
| Example 9 | 50% | | | 50% | 32.7% | 24.8% |
| Example 10 | | 10% | | 90% | 11.8% | 45.1% |
| Example 11 | | 40% | 60% | | 42.7% | 18.3% |
| Example 12 | 100% | | | | 59.3% | 22.0% |
| Example 13 | 100% | | | | 58.3% | |
| Example 14 | 100% | | | | 57.4% | |
| Example 15 | 75% | 25% | | | 62.6% | |
| Example 16 | 50% | 50% | | | 66.9% | |
| Example 17 | | 100% | | | 72.2% | |
| Example 18 | | 100% | | | 71.3% | |
| Example 19 | | 100% | | | 70.5% | |
| Comparative 1 | | 26% | | 74% | 46.0% | 37.0% |
| Comparative 2 | 58% | | | 42% | 25.0% | 45.0% |

| | Equivalent % of total acid equivalents | | | | |
|---|---|---|---|---|---|
| Polymer | Adipic Acid | Terephthalic Acid | 1,4-CHDA | Isostearic Acid | wt % diacid |
| Example 1 | 100% | | | | 45.6% |
| Example 2 | 100% | | | | 38.7% |
| Example 3 | | 100% | | | 41.8% |
| Example 4 | 100% | | | | 41.8% |
| Example 5 | 100% | | | | 45.4% |
| Example 6 | 100% | | | | 44.4% |
| Example 7 | 100% | | | | 44.7% |
| Example 8 | 100% | | | | 44.3% |
| Example 9 | 100% | | | | 42.5% |
| Example 10 | 100% | | | | 43.1% |
| Example 11 | 100% | | | | 39.0% |
| Example 12 | 50% | | 50% | | 18.7% |
| Example 13 | 25% | | 75% | | 41.7% |
| Example 14 | | | 100% | | 42.6% |
| Example 15 | 25% | | 75% | | 37.4% |
| Example 16 | 50% | | 50% | | 33.1% |
| Example 17 | 50% | | 50% | | 27.8% |
| Example 18 | 25% | | 75% | | 28.7% |
| Example 19 | | | 100% | | 29.5% |
| Comparative 1 | | | 100% | | 17.0% |
| Comparative 2 | 66% | 28% | | 6% | 27.0% |

Procedural:

The following procedures were used in testing the polymers of Examples 1-19 as well as comparative Examples 1 and 2.

Glass Transition Temperature—

Glass Transition Temperature was measured on a TA Instrument DSC 2920 according to ASTM Method D3418-99.

Tensile Testing—

Tensile testing was performed as follows—
1. A 20% solids ethanolic solution of the polymer was made.
2. The solution was poured into a 1.5 mm thick mold for an ASTM No. 4 dog bone with a testing area of 6.35 mm×38.10 mm.
3. The sample was allowed to dry at room temperature for 20 hours, then 20 hours at 60° C.
4. The sample was conditioned at 80% RH for 24-48 hours, then removed and immediately tested.
5. Measurement was conducted on an MTS Synergie 200 using a 50N load cell, and a tensile speed of 50 mm/min.

Diastron Hair Swatch Stiffness Procedure—

"Stiffness" is the amount of work required to deflect a hair swatch 10 mm at a rate of 50 mm/min. Stiffness is measured using the following procedure—

Five 6-inch virgin brown hair swatches are used for each sample to be tested. Polymer solids are set at 0.75% for each formulation, and 2 g of a 55% ethanol/water polymer solution is applied to each hair swatch. Each swatch is tared and then dipped into the aqueous polymer solution so that it is wetted thoroughly. The swatches are then drawn between the thumb and forefinger and blotted with a paper towel until the weight of each swatch is 2.0 g plus or minus 0.1 g more than the tare weight. The excess weight is the weight of the solution applied to the swatch and equates to 0.015 g of polymer applied to the hair swatch. After the solution is applied, the swatches are allowed to air dry in a constant temperature and humidity room, maintained at 22.2° C. (72° F.) and 50% relative humidity, prior to testing.

The swatches are tested the next day using a Diastron MTT 160 miniature tensile tester with a stiffness testing jig available from the manufacturer of the instrument. Each hair swatch is then laid across two lower horizontal prongs (or bars) separated by 10 cm and running perpendicular to direction the hair is laid to be evaluated one swatch at a time. The Diastron instrument then applies a measured force, in Newtons, with a 1 cm diameter horizontal bar perpendicular to the horizontal swatch and between the two lower bars to bend the swatch a distance of 10 mm. The work, in joules, is the stiffness of the hair swatch with a certain composition applied to the hair swatch. The stiffness for the five 6-inch swatches are then recorded and analyzed statistically to determine an average stiffness for the sample tested.

High Humidity Curl Retention

It is known that high humidity curl retention is a measurement of how well a fixative formulation will maintain hair in a given style in high humidity conditions and is a standard and important test of a hair fixative's performance. Nine 7.25-inch virgin brown hair swatches are used for each hair fixative sample to be tested. The curl retention properties of hair fixative polymers of the present invention are compared to each other, as well as commercial benchmarks. The test is conducted at 21° C. (70° F.) and 90% relative humidity over a period of 24 hours. The procedure allows for statistical analysis of formulation variables.

High Humidity Curl Retention Procedure—
1. Wet hair and comb through to remove snarls.
2. Squeeze out excess water by running the swatch between thumb and index finger.
3. Curl hair into a coil configuration by rolling it on a 3" long–½" diameter Teflon mandrel. Secure hair on mandrel with plastic clips.
4. Dry hair, mandrel and clip at 48.9° C. (120° F.).
5. When hair is dry and cool, carefully remove clips and hair curl from the mandrel.
6. Suspend hair from the bound end. Apply a controlled amount of hair spray in a controlled manner. In evaluating a non-aerosol hair spray, 4 bursts are evenly applied to both the front and back of the curl from a distance of 6 inches.
7. Lay the freshly sprayed curl on a horizontal surface and dry at 48.9° C. (120° F.) for 1 hour.
8. Suspend the dry curls in a random fashion from graduated, clear, transparent, plexiglass curl retention boards.
9. Take initial curl height reading $L_0$ and set curl retention boards into the environmental chamber.
10. Record curl length $L_t$ at 15, 30, 60, and 90 minute, 2, 3, 4, 5 and 24 hour intervals.

Percentage curl retention is calculated by the following formula:

$$\text{Curl Retention \%} = 100 \times (L-L_t)/(L-L_0)$$

where L=length of hair fully extended, $L_0$=initial curl length, $L_t$=curl length at a given time t.

TABLE 2

POLYMER EVALUTION BASED ON THE PRECEDING TEST PROCEDURES

| Polymer | Tg(° C.) | % elongation to break | Modulus (kgf/cm2) | Hair Swatch Stiffness (joules) | 2 hr Curl Retention (see #1) (%) | 24 hr Curl Retention (see #1) (%) | Minimum EtOH Solubility |
|---|---|---|---|---|---|---|---|
| Example 1 | 54 | 27% | 59 | 0.010 | 34% | 7% | <13% |
| Example 2 | 19 | too soft to run | too soft to run | 0.003 | 31% | 10% | <20% |
| Example 3 | 59 | 7% | 981 | 0.009 | 92% | 19% | 44% |
| Example 4 | 101 | 13% | 227 | 0.015 | 72% | 7% | 35% |
| Example 5 | 131 | too brittle to run | too brittle to run | 0.009 | 82% | 59% | 57% |
| Example 6 | unclear | 7% | 600 | 0.011 | 96% | 92% | 58% |
| Example 7 | 102 | too brittle to run | too brittle to run | 0.010 | 95% | 86% | 48% |
| Example 8 | 61 | 7% | 1191 | 0.011 | 95% | 74% | 56% |
| Example 9 | 65 | too soft to run | too soft to run | 0.003 | 51% | 11% | 46% |
| Example 10 | 104 | too brittle to run | too brittle to run | 0.011 | 97% | 95% | 45% |
| Example 11 | 32 | 33% | 94 | 0.008 | 50% | 10% | 28% |
| Example 12 | 50 | too brittle to run | too brittle to run | 0.009 | 91% | 71% | 35% |
| Example 13 | 39 | 13% | 184 | 0.015 | 87% | 8% | 39% |
| Example 14 | 70 | (see #2) | (see #2) | (see #3) | (see #4) | (see #4) | insoluble |
| Example 15 | 30 | 20% | 357 | 0.008 | 95% | 91% | 32% |
| Example 16 | −4 | 33% | 30 | 0.009 | 31% | 8% | 31% |
| Example 17 | 36 | too soft to run | too soft to run | 0.005 | 22% | 10% | 37% |
| Example 18 | 75 | 33% | 127 | 0.010 | 77% | 14% | 36% |
| Example 19 | 96 | 20% | 324 | 0.009 | 96% | 93% | 39% |
| Comparative 1 | unclear | (see #2) | (see #2) | (see #3) | (see #4) | (see #4) | insoluble |
| Comparative 2 | 78 | 27% | 536 | 0.007 (see #5) | (see #4) | (see #4) | 79% |

[1]Curl retention was determined using a 55% VOC non-aerosol hairspray.
[2]Tensile testing was not determined because the polymer did not dissolve in either ethanol or ethanol/water.
[3]Hair swatch stiffness was not determined because the polymer would not dissolve in either ethanol/water or ethanol.
[4]Curl retention was not determined because the polymer would not dissolve in the 55% ethanol/water solution used to make the 55% VOC non-aerosol hairspray.
[5]Polymer was dissolved in 100% ethanol in order to be able to run the procedure.

Example 20-23

Aerosol Hair Spray Formulations

| Ingredients | Ex. 20 (wt %) | Ex. 21 (wt %) | Ex. 22 (wt %) | Ex. 23 (wt %) |
|---|---|---|---|---|
| Polyetheramide | 4.0 | 4.0 | 4.0 | 4.0 |
| Ethanol | 71.0 | 50.0 | 22.0 | 55.0 |
| Water | — | 16.0 | 41.0 | — |
| Propellant A-31 (Isobutane/propane) | 25.0 | 15.0 | — | — |
| DYMEL A (dimethyl ether) | — | 15.0 | 33.0 | — |
| DYMEL 152a (1,1-difluoroethane) | — | — | — | 41.0 |
| Total | 100 | 100 | 100 | 100 |

Procedural—
1. Combine ethanol and water (if present) with mixing to form solvent.
2. Add polyetheramide to solvent with mixing until a solution or dispersion is formed.

3. Fill solution/dispersion into the packaging and charge with propellant.

The polyetheramide polymers from EXAMPLES 1-19 were used in forming the above aerosol hair spray formulations of EXAMPLES 20-23. The resulting products function adequately as aerosol hair sprays. Formulations were also prepared utilizing 3 and 5 wt % polymer solids.

Example 24-26

Non-Aerosol Hair Spray Formulations

| Ingredient | Ex. 24 (wt %) | Ex. 25 (wt %) | Ex. 26 (wt %) |
|---|---|---|---|
| Polyetheramide | 4.0 | 4.0 | 4.0 |
| Ethanol | 96.0 | 80.0 | 55.0 |
| Water | — | 16.0 | 41.0 |
| Total | 100 | 100 | 100 |

Procedural—
1. Combine the ethanol and water (if present) with mixing to form solvent.
2. Add the polyetheramide to solvent with mixing until a solution or dispersion is formed.
3. Fill solution/dispersion into the packaging.

The polyetheramide polymers from EXAMPLES 1-19 were used in forming the above non-aerosol hair spray formulations of EXAMPLES 24-26 and perform adequately as non-aerosol hair sprays. Formulations were also prepared utilizing 3 and 5 wt % polymer solids.

Although the present invention has been described and illustrated in detail, it is to be understood that the same is by way of illustration and example only, and is not to be taken as a limitation. The spirit and scope of the present invention are to be limited only by the terms of any claims presented hereafter.

We claim:
1. A personal care composition comprising a polyetheramide polymer comprising the following structure

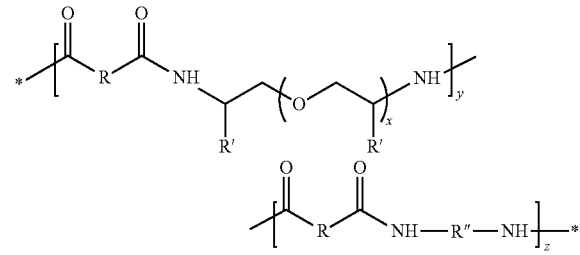

wherein R is aliphatic or aromatic; R' is hydrogen or $CH_3$; R" is aliphatic, or aromatic; x is 2 to 34; y is 1 to 250; and z is 0 to 350;
and a solvent,
wherein the polymer forms low viscosity solutions and or dispersions of less than about 35 centipoises in the solvent at about 6 weight percent polymer at about 25° C., and
wherein the solvent is an alcohol or alcohol-water blend.

2. The personal care composition according to claim 1 wherein the polymer does not have a 100% modulus between about 8 and 40 kgf/cm².

3. The personal care composition according to claim 1 wherein the composition is a hair fixative composition and the polymer provides curl retention of greater than about 30 percent after 2 hours at 21° C. and 90% humidity.

4. The personal care composition according to claim 1 wherein the composition is a hair fixative composition and the polymer provides a hair swatch stiffness of from about 0.005 to about 0.020 joules.

5. The personal care composition according to claim 3 wherein the hair fixative composition is a hair spray composition.

6. The personal care composition according to claim 1 wherein the alcohol is ethanol.

7. A process for preparing the personal care composition of claim 1 comprising:
reacting a mixture of from about 5 to about 85 weight percent of one or more poly(alkyleneoxy) diamines with from about 15 to about 95 weight percent of one or more diacids, weight percent based upon total weight percent of the polymer, and
dissolving or dispersing the resultant polyetheramide polymer in the solvent,
wherein a 6 weight percent solution or dispersion of the polyetheramide polymer in alcohol at about 25° C. has a viscosity of less than about 35 centipoise.

8. The process according to claim 7 wherein the reaction step further includes the reaction of from about 5 to about 50 weight percent of one or more diamines in addition to the one or more poly(alkyleneoxy) diamines.

9. The process according to claim 7 further comprising dissolving or dispersing other additives in the solvent in addition to the polymer.

10. The process according to claim 9 wherein the other additives comprise plasticizers, actives, neutralizers, colors or fragrances.

11. The process according to claim 7 wherein the reaction mixture does not have any mono-functional reactants that would react with either the amine or the acid groups.

12. The polyetheramide polymer of claim 1 wherein R is a linear aliphatic group.

13. The polyetheramide polymer of claim 12 wherein the linear aliphatic group is selected from the group consisting of 1,4-butane, 1,6-hexane acid, 1,7-heptane, 1,8-octane, 1,9-nonane, 1,10-decane, 1,12dodecane, 1,13-tridecane and 1,14-tetradecane.

14. The polyetheramide polymers of claim 1 wherein R is an aromatic group.

15. The polyetheramide polymer of claim 1, wherein the polymer is formed from an aromatic diacid selected from the group consisting of phthalic, isophthalic and terephthalic acid.

16. The solvent of claim 1 wherein the alcohol-water blend is an ethanol-water mix and the ethanol is present from about 50 to about 70 percent.

17. The solvent of claim 1 wherein the alcohol-water blend is an ethanol-water mix and the ethanol is present from about 55 to about 65 percent.

* * * * *

UNITED STATES PATENT AND TRADEMARK OFFICE
CERTIFICATE OF CORRECTION

| | | |
|---|---|---|
| PATENT NO. | : 7,919,074 B2 | Page 1 of 1 |
| APPLICATION NO. | : 11/419010 | |
| DATED | : April 5, 2011 | |
| INVENTOR(S) | : Michael Philbin et al. | |

It is certified that error appears in the above-identified patent and that said Letters Patent is hereby corrected as shown below:

Col. 30, line 46, delete "acid" after 1,6-hexane

Signed and Sealed this
Second Day of August, 2011

David J. Kappos
*Director of the United States Patent and Trademark Office*